United States Patent
Erwin et al.

(10) Patent No.: US 10,835,406 B2
(45) Date of Patent: Nov. 17, 2020

(54) ADJUSTABLE WRIST BRACE

(71) Applicant: Ortho Systems, Agoura Hills, CA (US)

(72) Inventors: Edwin Erwin, Studio City, CA (US);
Zhuang Shao, Los Angeles, CA (US);
Kenji Watabe, Ventura, CA (US);
Tracy E. Grim, Thousand Oaks, CA (US)

(73) Assignee: Ortho Systems, Agoura Hills, CA (US)

( * ) Notice: Subject to any disclaimer, the term of this patent is extended or adjusted under 35 U.S.C. 154(b) by 55 days.

(21) Appl. No.: 15/253,777

(22) Filed: Aug. 31, 2016

(65) Prior Publication Data

US 2018/0055672 A1    Mar. 1, 2018

(51) Int. Cl.
*A61F 5/01* (2006.01)
*A61F 5/058* (2006.01)

(52) U.S. Cl.
CPC ........ *A61F 5/0118* (2013.01); *A61F 5/05866* (2013.01); *A61F 2005/0186* (2013.01)

(58) Field of Classification Search
CPC ........ A61F 5/0118; A61F 5/01; A61F 5/0102; A61F 5/0104; A61F 5/013; A61F 5/05866; A61F 5/05858; A61F 5/05841; A61F 5/058; A61F 5/05; A41D 19/01582; A41D 13/081
USPC ............. 602/20–22; 128/878–879; 2/16, 162
See application file for complete search history.

(56) References Cited

U.S. PATENT DOCUMENTS

| | | | |
|---|---|---|---|
| 4,584,993 A | 4/1986 | Nelson | |
| 5,092,318 A | 3/1992 | More et al. | |
| 5,267,943 A * | 12/1993 | Dancyger | A61F 5/0118 602/20 |
| 5,759,166 A * | 6/1998 | Nelson | A61F 5/0118 602/21 |
| 6,186,969 B1 * | 2/2001 | Bell | A61F 5/0118 602/64 |
| 6,196,985 B1 * | 3/2001 | Slautterback | A61F 5/05866 128/880 |
| 6,561,994 B1 * | 5/2003 | Mills | A61F 5/0118 602/20 |
| 6,790,192 B2 | 9/2004 | Robinson | |
| 6,893,410 B1 | 5/2005 | Hely | |
| 7,318,812 B2 * | 1/2008 | Taylor | A61F 5/0118 602/21 |
| 7,862,527 B2 | 1/2011 | Gramza et al. | |
| 8,114,041 B2 * | 2/2012 | Wyatt | A61F 5/0118 128/846 |
| 8,147,438 B2 | 4/2012 | Livolsi et al. | |

(Continued)

OTHER PUBLICATIONS

International Search Report and Written Opinion dated Dec. 6, 2017, regarding PCT/US2017/047402.

*Primary Examiner* — Rachel E Bredefeld
*Assistant Examiner* — Caitlin A Carreiro
(74) *Attorney, Agent, or Firm* — Fulwider Patton LLP (57) ABSTRACT

Some aspects of the present disclosure describe an orthopedic brace for a portion of a user's upper extremity distal to the elbow. The orthopedic brace includes a body configured to surround said portion of the user's upper extremity. The body includes a first region configured to stabilize said portion of the user's upper extremity. The orthopedic brace includes a second region coupled to the first region. The second region has sufficient elasticity to enable the body to adjust circumferentially to fit said portion of the user's upper extremity.

6 Claims, 11 Drawing Sheets

(56) References Cited

U.S. PATENT DOCUMENTS

| | | | |
|---|---|---|---|
| 9,486,351 B2* | 11/2016 | Pegg | A61F 5/013 |
| 2003/0083605 A1* | 5/2003 | Edmund | A61F 5/0109 |
| | | | 602/60 |
| 2004/0049141 A1* | 3/2004 | Slautterback | A61F 5/0118 |
| | | | 602/21 |
| 2011/0105978 A1* | 5/2011 | Hou | B32B 5/04 |
| | | | 602/75 |
| 2012/0010547 A1 | 1/2012 | Hinds | |
| 2012/0165714 A1 | 6/2012 | Forbes et al. | |
| 2013/0211304 A1 | 8/2013 | Romo et al. | |
| 2014/0074004 A1* | 3/2014 | Lopez | A61F 5/0111 |
| | | | 602/28 |

* cited by examiner

ADJUSTABLE WRIST BRACE

BACKGROUND

Field

The present disclosure relates generally to an adjustable wrist brace or thumb spica, and more particularly, to an adjustable wrist support having an elastic portion configured to accommodate several different size users.

Background

A fixating support, such as a wrist brace or thumb spica, is used to provide compression and support for wrist, thumb, hand and forearm for management of post fracture or soft tissue injuries and other conditions. In the wrist brace, the thumb protrudes through a thumbhole to allow function of the thumb, while the wrist is immobilized or fixated by a support structure to promote healing. Typically, a wrist brace includes a body portion that is made of one or more materials having the same flexibility and/or binding with minimal flexibility and attachment members that hold the body portion of the brace tight against the user's wrist to maintain immobility. Thumb spicas suffer from similar problems in that they often only provide a preset diameter that a user slips his/her thumb through or are difficult attempt a difficult one-size-fits all approach by using a single Velcro strap that is cumbersome. However, such configurations only accommodates a limited size range necessitating the need for a multitude of sizes to fit all users or are simply too difficult to get a good fit. Moreover, an injured wrist may also exhibit some swelling. The swelling may change depending on the user's activities and as the wrist heals over time. In the prior art configurations, as the wrist heals and swelling reduces, the wrist brace may become too large. Also swelling may increase initially with activity or dependence. This requires the wearer to purchase an additional wrist brace to continue the healing process and could not accommodate different swelling patterns associated with an injured wrist and a user's daily activities.

Figure 1:
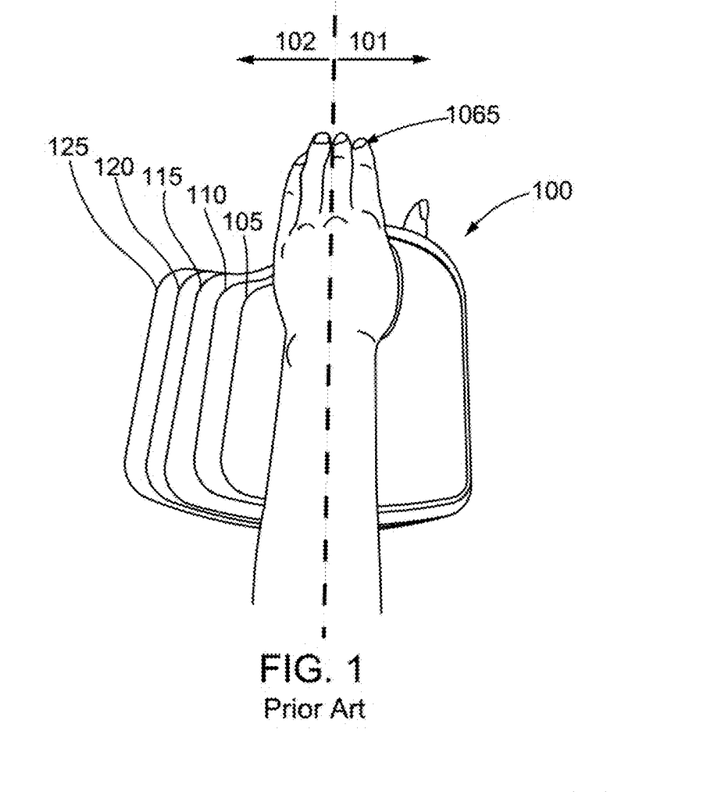
FIG. 1 illustrates the left flat pattern of the conventional sizing of current wrist brace in relation to a left hand with the radial and ulnar regions.

For instance, FIG. 1 illustrates the left flat pattern of the conventional sizing of current wrist brace 100. As shown, the brace 100 includes radial region 101 and ulnar region 102 in relation to a user's left hand 1065. FIG. 1 illustrates five different sizes 105-125 of a wrist brace, which are necessary, in the prior art, to accommodate the majority of brace wearers. As shown, the most significant size difference is primarily in the ulnar region 102.

Some wrist braces have attempted to include features to adjust to a user's wrist size. However, these braces are not intuitive, have additional removable straps that require adjustment, require special instructions, and are simply cumbersome to use and size appropriately.

Therefore, it is difficult to design a wrist brace and/or thumb spica capable of accommodating several wrist sizes, negating the need for a multitude of wrist braces of different sizes of limited adjustability.

SUMMARY

Some aspects of the present disclosure describe an orthopedic brace for a portion of a user's upper extremity distal to the elbow. The orthopedic brace includes a body configured to surround said portion of the user's upper extremity. The body includes a first region configured to stabilize said portion of the user's upper extremity. The orthopedic brace includes a second region coupled to the first region. The second region has sufficient elasticity to enable the body to adjust circumferentially to fit said portion of the user's upper extremity.

Another aspect of the present disclosure includes a method of applying an orthopedic brace to a portion of a user's upper extremity distal to the elbow. The orthopedic brace includes a body having a first region to stabilize said portion of the user's upper extremity and second region coupled to the first region. The second region has sufficient elasticity to enable the body to adjust circumferentially to fit said portion of the user's upper extremity. The method includes surrounding said portion of the user's upper extremity with the body. The first region stabilizes said portion of the user's upper extremity and the second region adjusts the body circumferentially to fit said portion of the user's upper extremity when said portion of the user's upper extremity is surrounded by the body.

It is understood that other aspects of the present invention will become readily apparent to those skilled in the art from the following detailed description, wherein it is shown and described only exemplary configurations of a wrist brace by way of illustration. As will be realized, the present invention includes other and different aspects of a wrist brace and its several details are capable of modification in various other respects, all without departing from the spirit and scope of the present invention. Accordingly, the drawings and the detailed description are to be regarded as illustrative in nature and not as restrictive.

BRIEF DESCRIPTION OF THE DRAWINGS

Various aspects of the present invention are illustrated by way of example, and not by way of limitation, in the accompanying drawings, wherein.

DETAILED DESCRIPTION

The detailed description set forth below in connection with the appended drawings is intended as a description of various exemplary embodiments of the present invention and is not intended to represent the only embodiments in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present invention. Acronyms and other descriptive terminology may be used merely for convenience and clarity and are not intended to limit the scope of the invention The word "exemplary" is used herein to mean serving as an example, instance, or illustration. Any embodiment described herein as "exemplary" is not necessarily to be construed as preferred or advantageous over other embodiments. Likewise, the term "embodiment" of an apparatus does not require that all embodiments of the invention include the described components, structure, features, functionality, processes, advantages, benefits, or modes of operation.

The terms "connected," "coupled," "joined" or any variant thereof, mean any connection or coupling, either direct or indirect, between two or more elements, and can encompass the presence of one or more intermediate elements between two elements that are "connected," "coupled," or "joined" together.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure.

Various aspects of an orthopedic brace will now be presented. However, as those skilled in the art will readily appreciate, these aspects may be extended to other orthopedic braces without departing from the spirit and scope of the invention. More specifically, the various aspects of a wrist brace presented throughout this disclosure are applicable to any suitable wrist brace or fixating support providing anatomical support to any portion of an upper extremity distal to a user's elbow, including by way of example, a brace used to support a hand, wrist, thumb, and/or an upper portion of a forearm.

The orthopedic brace may include a thumb spica. The thumb spica may utilize the same configuration as the orthopedic/wrist brace for immobilizing a user's thumb, while simultaneously ensuring a proper fit. The thumb spica may be attached to the wrist brace or a separate orthopedic brace designed only for use with a user's thumb.

Various elastic materials for use with a wrist brace are disclosed. For the purposes of this disclosure, an elastic material is a material that stretches beyond its stationary size. For instance, the elastic material may enable a wrist brace to expand between 5 and 100 mm larger than its original size, either laterally or longitudinally. Such an expansion may accommodate more than one of the brace sizes illustrated in FIG. 1, negating the need for multiple sizing patterns required by the prior art.

An elastic material may also be a thread or binding that exhibits the same stretching property discussed above.

The various concepts presented throughout this disclosure are well suited for wrist braces to provide adjustability without requiring numerous sizing options and to accommodate growth and reduction in swelling as a wrist heals. However, as those skilled in the art will readily appreciate, these concepts are not limited to wrist braces or thumb spicas.

Figure 2:
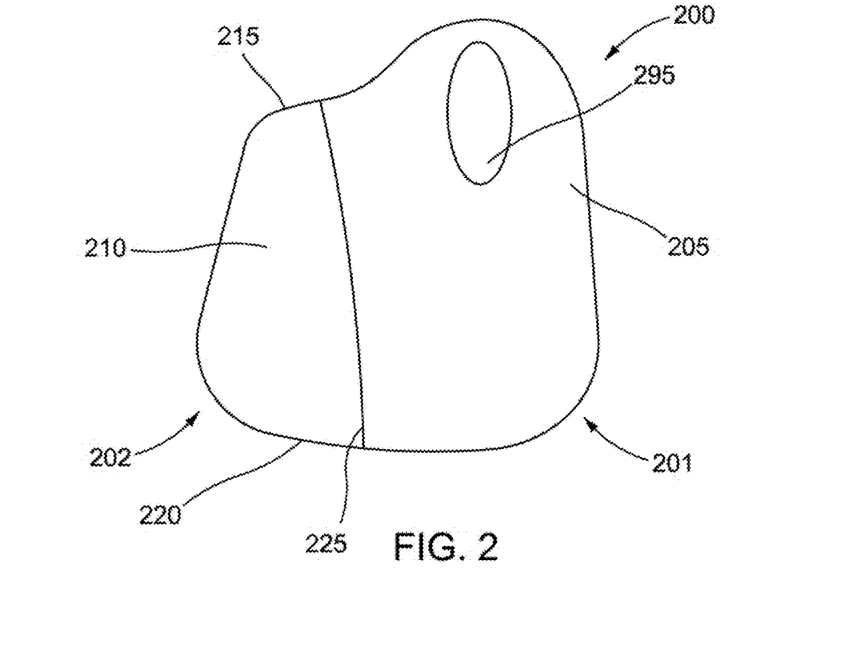
FIG. 2 illustrates a plan view of an exemplary adjustable wrist brace body.

The elastic material may be a region that is comprised in a portion of the wrist brace body. Such a region may comprise a foam, such as open-cell foam, configured stretch at a range between 110% and 300% from its original shape. Additionally, a synthetic elastic material with significant stretch/elasticity may be laminated or attached to both sides of the interior and/or exterior sides of the foam. For instance Lycra® is a material that provides significant stretch and may be used as a laminate for the exterior and interior sides of the foam. However, one of ordinary skill in the art will appreciate that the elastic material is not limited to the materials discussed above. In fact any material with suitable stretch or elasticity may be used without departing from the scope of the invention. Elasticity and flexibility may be used interchangeably in this disclosure. Elasticity or flexibility is defined as a material that is able to expand from its original size when manually or mechanically pulled upon. A material may have lateral and/or longitudinal flexibility. The amount of flexibility is defined by the size the material is capable of stretching from its original size or by a percentage that it is capable of stretching from its original size FIG. 2 illustrates a plan view of an exemplary adjustable wrist brace body 200. As shown, the brace 200 includes a distal region 215, a proximal side 220, a radial side 201 and ulnar side 202. The radial region 201 includes a thumb hole 295 and a region 205. The ulnar side 202 includes a region 210. As shown, the regions 205 and 210 are joined together at point 225. Each of the regions 205 and 210 may comprise a single continuous material. For the preferred embodiment, the region 210 may include greater flexibility than the region 205. As a result, the region 210 may stretch in a lateral and/or longitudinal direction to accommodate different sizes hands and/or wrists. However, in another aspect of the brace, the region 205 may have greater flexibility than the region 210. Alternatively, the region 210 may have greater flexibility than the region 205, in some aspects of the brace. When in use, the radial side 201 and the ulnar side 202 of the wrist brace may be connected by a dorsal locator (not shown). The dorsal locator may be made of a ribbed material such as cotton knit. The addition of the dorsal locator to the body 200 forms a cylinder that a user can comfortably fit his/her hand through during the process of applying the brace to the user's wrist.

The region 205 may be made of a material that is no stretch or reduced stretch. For instance, the region 205 may have less stretch (or flexibility) than the region 210. The region 205 may comprise open-cell foam with less elastic fabric lamination than the region 210.

The region 210 may be made of the elastic material described above. The configuration described in FIG. 2 allows the region 210 to expand on the proximal side 220 as well as the distal side 215. But as shown, the distal side 215 is slightly angled and the width/lateral distance of the region 210 is much smaller in relation to the proximal side 220 (greater than 90 deg). This configuration allows the proximal side 220 to expand as necessary to the girth of the forearm but limits the expansion on the distal side 215 for the hand. The purpose to bias the expansion to the forearm is the thought that the majority of different arm sizes apply more on the forearm rather than the hand. The advantage to limit expansion on the distal side 215 is to balance between the stability and expansion of the hand size. Moreover, incorporating a region 210 of greater of flexibility at the ulnar side 202, than the region 205, at the radial side 201 provides stability around the thumb hole 295 and the radial section 201. At the same time, the wrist brace may be configured to accommodate a plurality of sizes because of the incorporation of greater flexibility in the region 210, without impacting the strength and/or stability of the radial side 201 of the wrist brace. Thus, the wrist brace is capable of providing ample support while also accommodating a variety of wrist and/or hand sizes. As a result, a user may use a single brace to accommodate reduction/increase in swelling from the injured wrist and a store may require less inventory as a single adjustable wrist brace may be adjust to the size of two or more separate and different sized braces as described with respect to FIG. 1.

Figure 3:
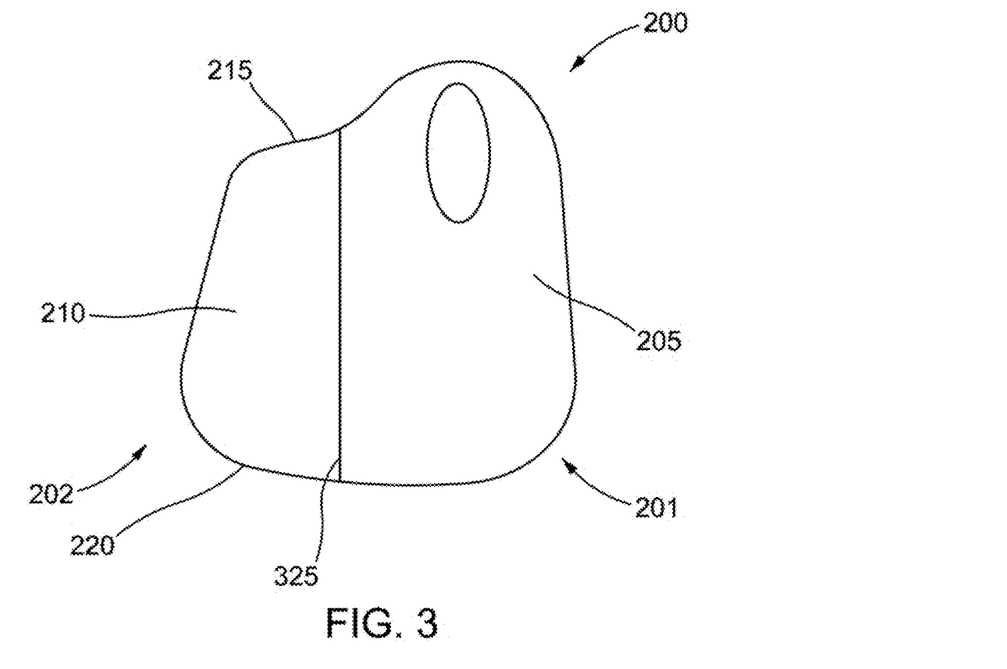
FIG. 3 illustrates a plan view of the exemplary adjustable wrist brace body having a different point at which the regions are joined.

FIG. 3 illustrates a plan view of the exemplary adjustable wrist brace body 200 having a different point 325 at which the regions 205 and 210 are joined. For instance, in FIG. 3, the regions 205 and 210 are joined along a vertical cut rather than the diagonal cut (greater than 90 degrees), as shown in FIG. 2. Thus, the distal side 215 has a similar or slightly smaller width/lateral distance of the region 210 in relation to the proximal side 220. This configuration allows the distal and proximal sides 215 and 220 to expand similarly to allow girth of the hand and the forearm. This configuration does not bias the expansion to either hand or forearm with respect to FIG. 1. This purpose is for allowing more distal expansion. For instance, users with a larger hand may require greater distal expansion. Furthermore, the distal expansion may assist in grabbing an object, which may be more comfortable with a brace capable of distal expansion.

Figure 4:
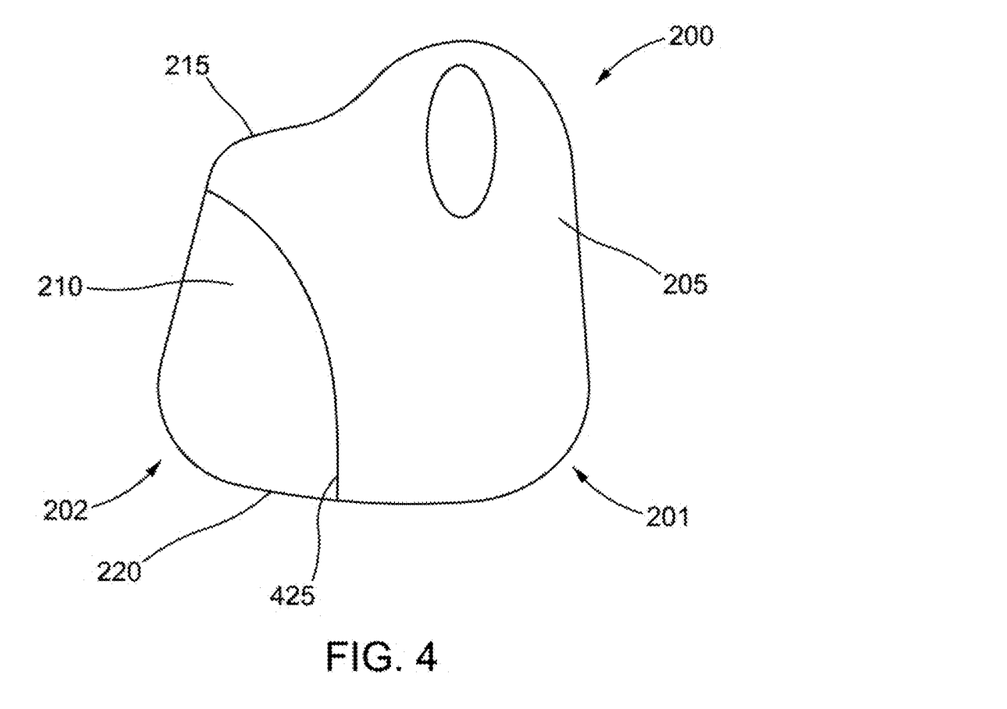
FIG. 4 illustrates a plan view of the exemplary adjustable wrist brace body having a differing regional configuration than the previous exemplary views.

FIG. 4 illustrates a plan view of the exemplary adjustable wrist brace body 200 having a differing region 210 configuration than the previous exemplary views. As show, the region 210 has a convex curve, which is joined at point 425 to a corresponding concave curve formed about the region 205. The configuration illustrated in FIG. 4 provides little or no expansion at the distal side 215 because the region 210 does not extend to the distal area. The region 205 covers the distal side 215. Such a configuration maintains stability at the distal side 215, while keeping the user's hand in place due using a material of lesser flexibility at the distal side 215.

Figure 5:
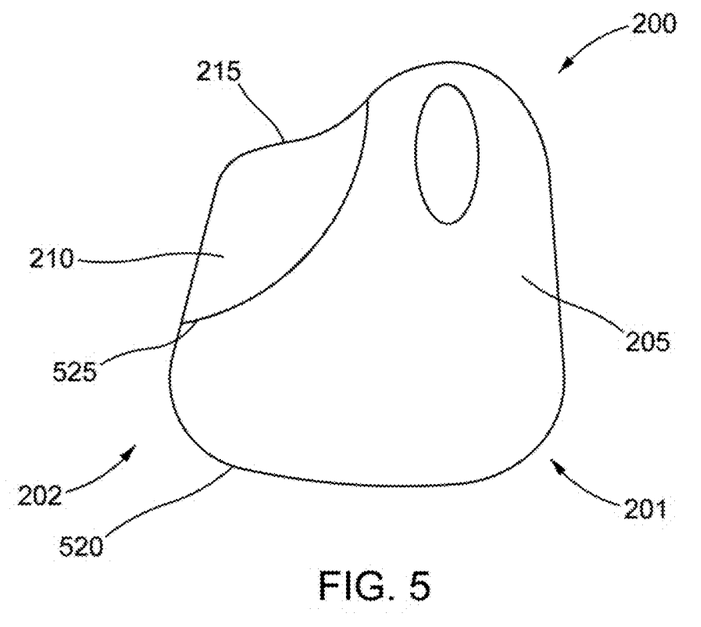
FIG. 5 illustrates a plan view of the exemplary adjustable wrist brace body having a differing regional configuration than the previous views.

FIG. 5 illustrates a plan view of the exemplary adjustable wrist brace body 200 having a differing region 210 configuration than the previous views. As shown, the region 210 is placed at the distal side 215, rather than the proximal side 220, as illustrated in FIG. 5 and joined together at point 525. For instance, this exemplary configuration provides less expansion along the proximal side 520 due to the use of material of lesser flexibility than the material used for the region 210. As a result, when a user of the brace spreads his/her hand to, for instance, grab an item, the distal side 215 will adjust to accommodate the hand expansion. Additionally, the proximal region 520 has greater stability, in this example, which may provide better forearm stability.

In some aspects of the adjustable wrist brace, the regions 205 and 210 may be joined by stitching, welding, gluing, or any other suitable means for connecting two materials such as the foams describe above. Conjunctively or conversely, the body of the wrist brace may be made of a single material rather than two distinct materials bound at a point. For instance stretch and non-stretch binding may be used to stabilize the radial side 201, while keeping the ulnar side 202 flexible with more flexibility in the binding to accommodate different hand/forearm sizes.

In some aspects of the wrist brace, the foam for the regions 205 and/or 210 may be die cut. Die cut edges of foam may wear out from excessive stretching. In order to prolong the life of the wrist brace, a stitch binding along the die cut edges of the foam may be utilized for additional strength and/or improved aesthetics. Different techniques may be used to add a binding to the perimeter of the region 210 to maintain greater flexibility, such as using an elastic or flexible binding. To maintain stability at the region 205, a non-elastic binding or binding of lesser flexibility than the binding around the perimeter of the region 210 may be utilized. Such techniques may control the location of the expansion of the wrist brace 200 as well as limit expansion of the wrist brace 200 in other locations.

Figure 6:
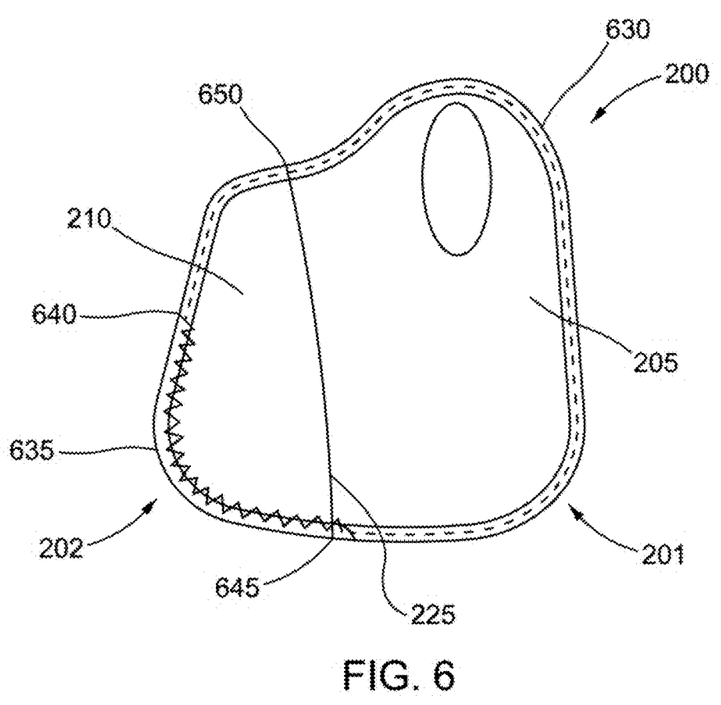
FIG. 6 illustrates a plan view of the exemplary adjustable wrist brace body with binding.

FIG. 6 illustrates a plan view of the exemplary adjustable wrist brace body 200 with binding. As shown, the view of the adjustable wrist brace 200 of FIG. 6 is similar in configuration to the adjustable wrist brace of FIG. 2. For instance, the adjustable wrist brace 200 of FIG. 6 incorporates the regions being joined at an angle at point 225. However, FIG. 6 also incorporates different binding materials as discussed above.

As shown, FIG. 6 includes binding materials 630 and 635, as well as binding edges 640, 645, and 650. The binding materials 630 and 635 are stitched to the edge of the body. The different materials or regions of varying flexibilities are bound by the binding edges to alter flexibility The binding material 635 may have greater flexibility than the binding material 630. The binding material 630 surrounds the entire external portion of the region 205 and a portion of the region 210. The binding material 630 is joined with the binding material 635 at the edges 640 and 645. The binding material 630 may be stitched to the regions 205 and/or 210 using a traditional or straight stitching method. The binding material 635 may be stitched to the region 205 and/or 210 using a zig-zag stitch method, which may provide additional stretch or flexibility than a straight stitch.

The binding 630 covers a portion of the region 210 from the edge 650 to the edge 640 along the ulnar side 202 of the wrist brace body 200. The edge 640 may be along the ulnar dorsal point of the user. The binding 635 and zig-zag stitch covers the region 210 from the edge 640 to the edge 645. This maintains the elastic properties of the region 210, at least in the region between the edges 640 and 645. Thus the ulnar (202) proximal region of the wrist brace body 200 will have a greater flexibility than the rest of the body 200.

However, the binding 630 that spans the region from the edges 640 to 650 has less flexibility than the binding 635. This reduces the amount of stretch of the region 210 in relation to the ulnar proximal region. As such, reducing the stretch in these particular regions keeps stability in the distal ulnar region.

Figure 7:
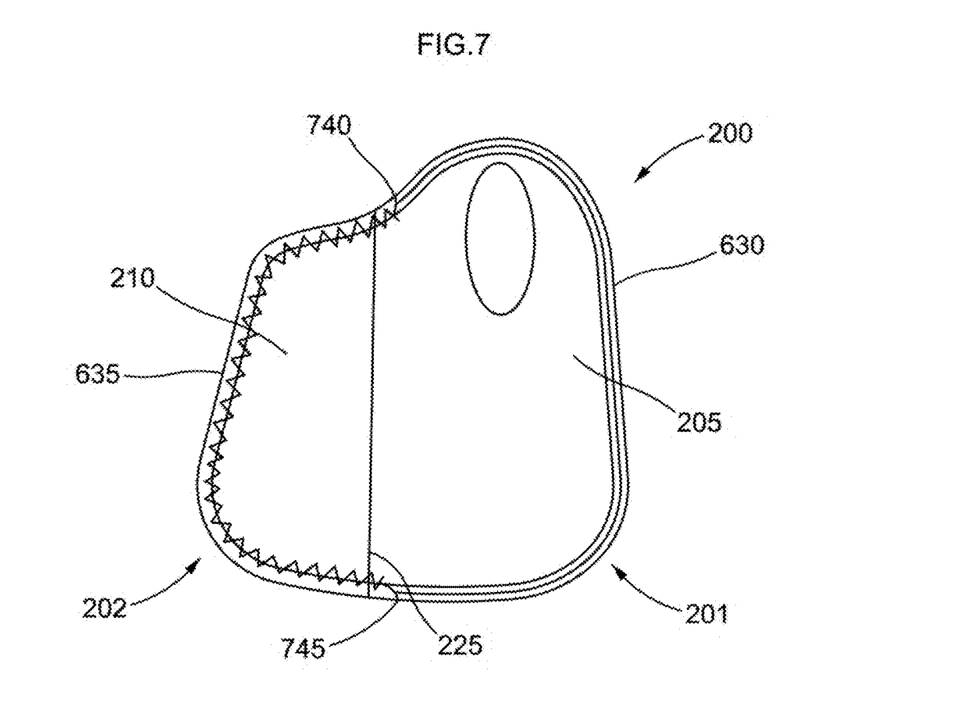
FIG. 7 illustrates a plan view of a different exemplary configuration of the binding along the wrist brace body.

FIG. 7 illustrates a plan view of a different exemplary configuration of the binding along the wrist brace body 200. As shown, the binding 635, attached by a zig-zag stitch, spans a region between edges 740 and 745. The binding 630 spans the region opposing the binding 635 and is bound by the same edges 740 and 745. In this exemplary view, the binding 635 may have greater flexibility than the binding 630. The binding 635 covers the exposed edges of the region 210, including the proximal and distal sides of the region 210. Such a configuration allows the wrist brace to adjust in size according to the girth of a user's hand and forearm. The binding 630 maintains stability on the radial side 201 of the body 200.

Figure 8:
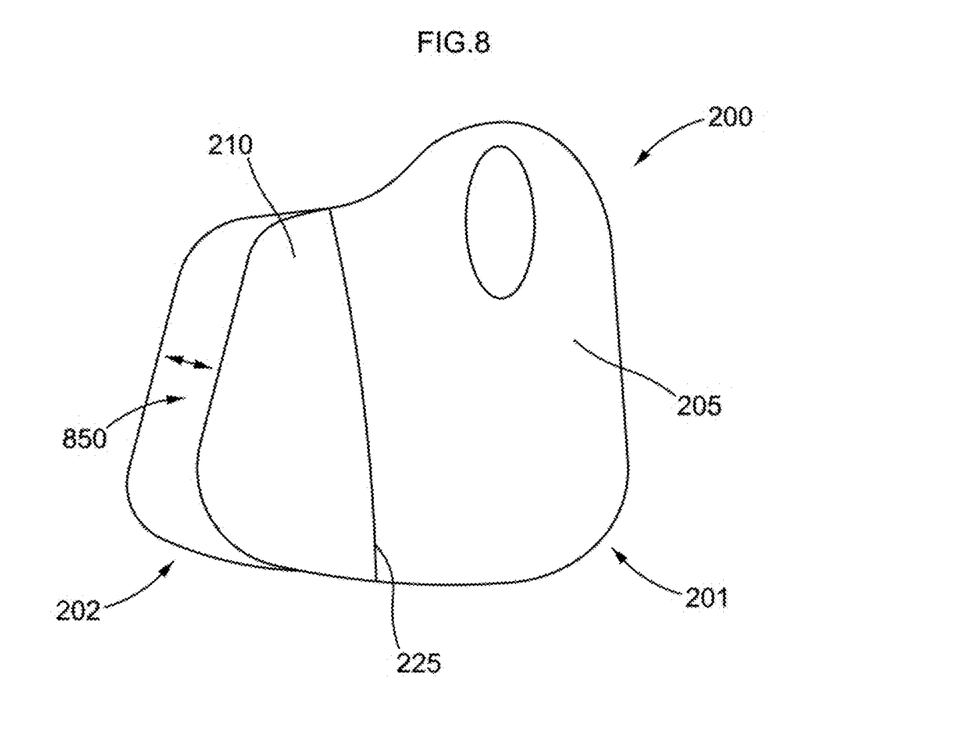
FIG. 8 illustrates the amount of stretch achieved by the exemplary configuration of the adjustable wrist brace.

FIG. 8 illustrates the amount of stretch achieved by the exemplary configuration of the adjustable wrist brace. In this example, the body 200 does not include a binding to adjust the region's stretch. However, one of ordinary skill in the art will appreciate that a binding such as the bindings discussed above may be used to achieve any desired configuration without departing from the scope of the invention.

As shown, the region 210 expands a distance 850 because of its elastic properties, which are greater than those of the region 205. In this example the region 210 may comprise open-cell foam and/or elastic fabric lamination. The distance 850 may be between 5-100 mm, which may equate to approximately a 200% expansion of the original, unstretched size of the region 210. By not utilizing any binding in this example, the region 210 has greater expandability to accommodate more wrist and/or hand sizes. Thus, the adjustable wrist brace body 200 may accommodate several at least 2 or more of the discrete sizes described in FIG. 1. In fact, traditional materials used for wrist braces are only capable of expanding between 5 mm and 10 mm, which equates to less than 110% expansion from the original un-stretched size.

Figure 9:
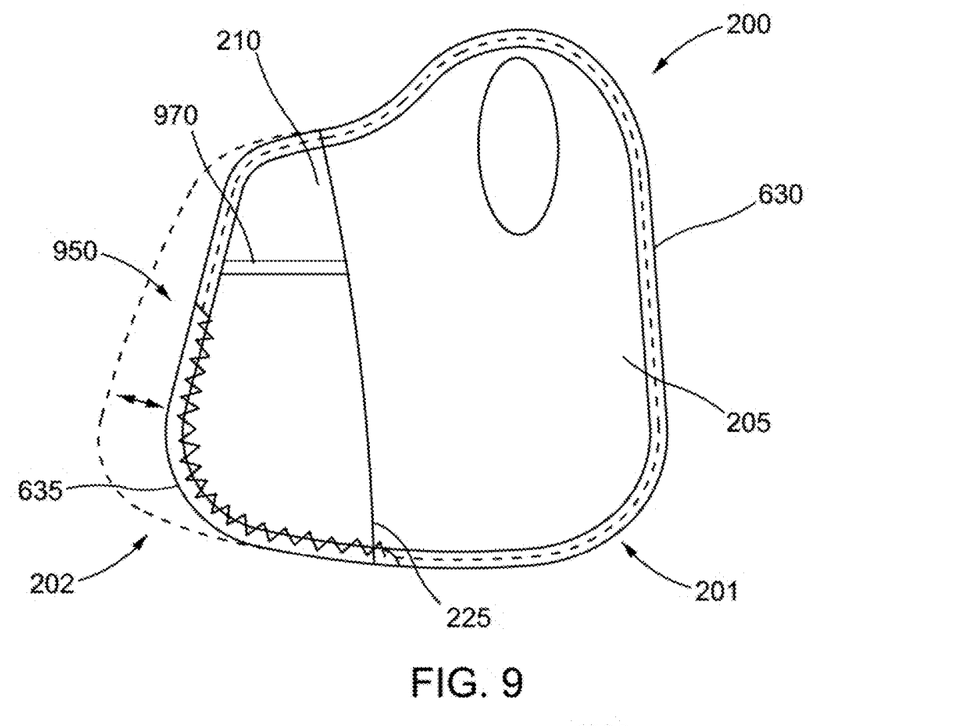
FIG. 9 illustrates of adjusting the stretch achieved by the exemplary configuration of the adjustable wrist brace by incorporating a binding.

However, the use of binding(s) may increase stability in the wrist brace, without compromising the adjustability of the wrist brace. For instance, FIG. 9 illustrates of adjusting the stretch achieved by the exemplary configuration of the adjustable wrist brace by incorporating a binding. As shown, the region 210 has a less uniform stretch pattern 950 than the stretch pattern illustrated in FIG. 8. For instance, the stretch pattern 950 may comprise more stretch in the proximal region and less stretch in the distal region. This increases stability and control in the distal region, while allowing the proximal region to adjust to a user's forearm size. In addition, the stretch in the distal region accommodates some user hand movements, such as grabbing and object, while still maintaining stability in the wrist brace. Or other means for increasing stability and control the stretch of region 210 can be in a form of one or more non-stretch or less stretch materials 970 acting like a bridge laterally connecting the lateral edges of the region 210. The non-stretch or less stretch bridge materials may also be the independent from the binding configurations (not shown).

As shown in FIG. 9, the region 210 is capable of stretching approximately 5 mm-70 mm, or approximately 150% of its original un-stretched size. Thus, the binding reduces stretch on the ulnar side 202 for greater stability in the wrist brace.

The wrist brace of the present invention provides a simple way to adjust the size of the brace with few parts, minimal steps, adjustment of extraneous parts, and without any need for training. For instance, the wrist brace self-adjusts by expanding the body of the brace laterally relative to a user's hand and/or forearm size. In doing so, the body of the brace may stay neutral relative to the user's hand for simplicity and automatically expand as attachment members applied around the user's wrist. As the attachment members are applied, the attachment member locks the expansion of the body to the adjusted size. This locking feature gives stability in the brace.

Figure 10:
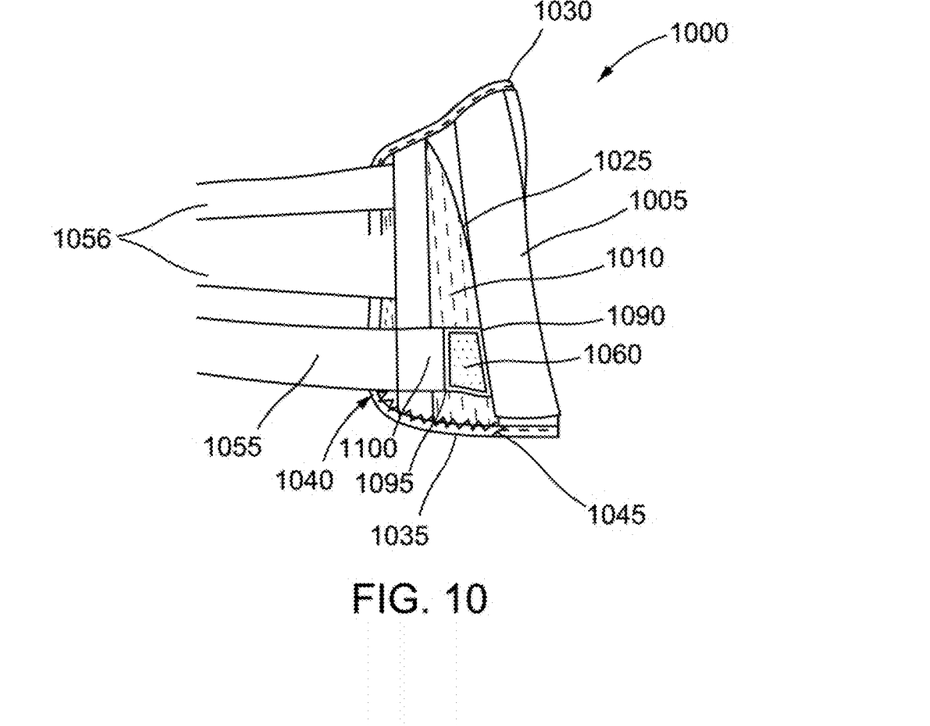
FIG. 10 illustrates a side view of an exemplary wrist brace having features that enable the brace to adjust to the user's forearm/hand in a simple fashion.

FIG. 10 illustrates a side view of an exemplary wrist brace 1000 having features that enable the brace to adjust to the user's forearm/hand in a simple fashion. FIG. 10 includes a wrist brace 1000, which may have a body similar to the body 200 discussed with respect to the figures above. The brace 1000 includes a body have regions 1005 and 1010. The region 1010 may have greater flexibility than the region 1005. Similar to the above figures, the regions 1005 and 1010 are joined together at point 1025. The body also includes bindings 1030 and 1035. The binding 1035 may have greater flexibility than the binding 1030. The binding 1035 may span the region between edges 1040 and 1045. The binding 1030 may span the region opposite the region covered by the binding 1035. The wrist brace also includes attachment members 1056 and stabilizer attachment member 1055. Attachment members 1056 has a first end and a free end. The stabilizer attachment member 1055 has a first end and a free end. The free end defined here is any part of the attachment member after the first end. A hook section 1060 has two ends 1090 and 1095. The first end 1090 of the hook section 1060 is attached to the region 1005. In some aspects of the brace, second end 1095 of the hook section 1060 may be independent from the stabilizer attachment member 1055. Alternatively, second end 1095 of the hook section 1060 may be attached to the first end of the stabilizer attachment member 1055. Additionally, the first end of attachment members 1056 may attach to the elastic region 1010, while the first end of the stabilizer attachment member may also attached 1010 or the second end of the hook section 1060. Elastic band 1100 may attach to the first end of the stabilizer attachment member and to the second end of the 1095 of hook 1060.

Figure 11:
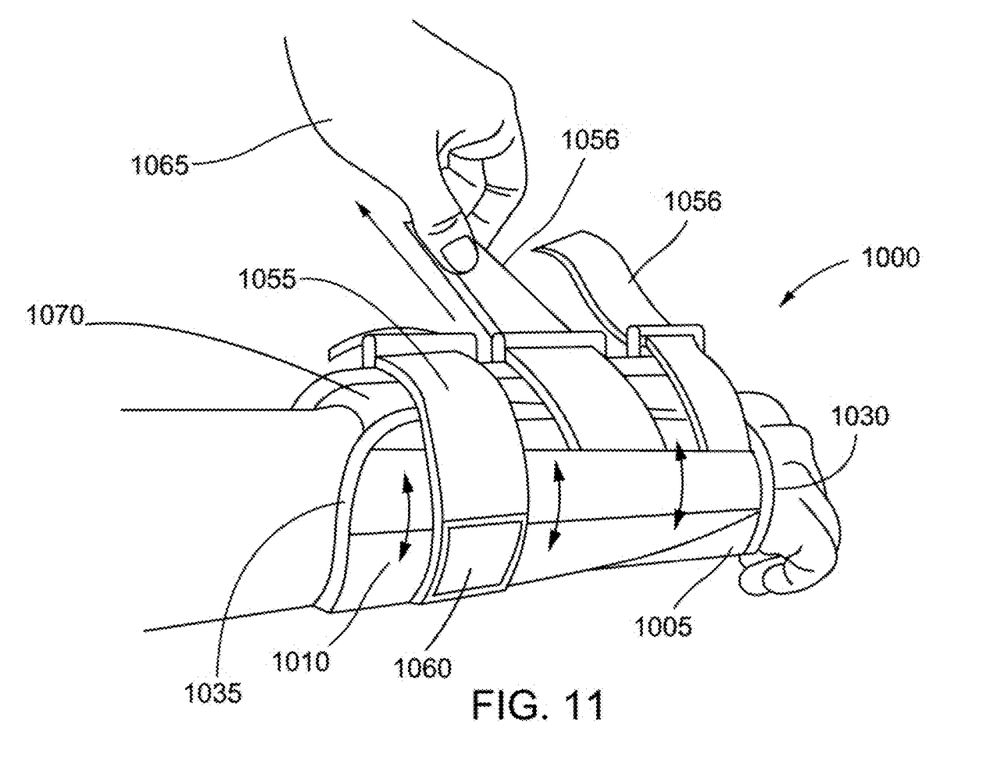
FIG. 11 illustrates applying the exemplary wrist brace to the user's wrist.

FIG. 11 illustrates applying the exemplary wrist brace 1000 to the user's wrist. As shown, the free end of attachment member 1056 receives a pulling motion from a user 1065 to tighten the brace 1000. The attachment member may be pulled across a dorsal locator 1070 positioned between the two ends of the body of the wrist brace. In some aspects of the brace, the body of the wrist brace may automatically expand while the user puts on the brace and/or tighten the free end of attachment member(s) 1056 or 1055. By automatically expanding in this manner, the wrist brace is capable of adjusting to accommodate the user's size with minimal effort. Thus, applying the brace to the user's wrist is simplified by the configuration discussed above. In fact, the user can simply tighten the brace with one hand, while the elastic region 1010 expands laterally to accommodate the user's forearm and/or hand as the user tightens the free end of attachment members 1056 and 1055 around a closure system. The closure system may comprise a D-ring and hook & loop or lace with hook & loop.

Figure 12:
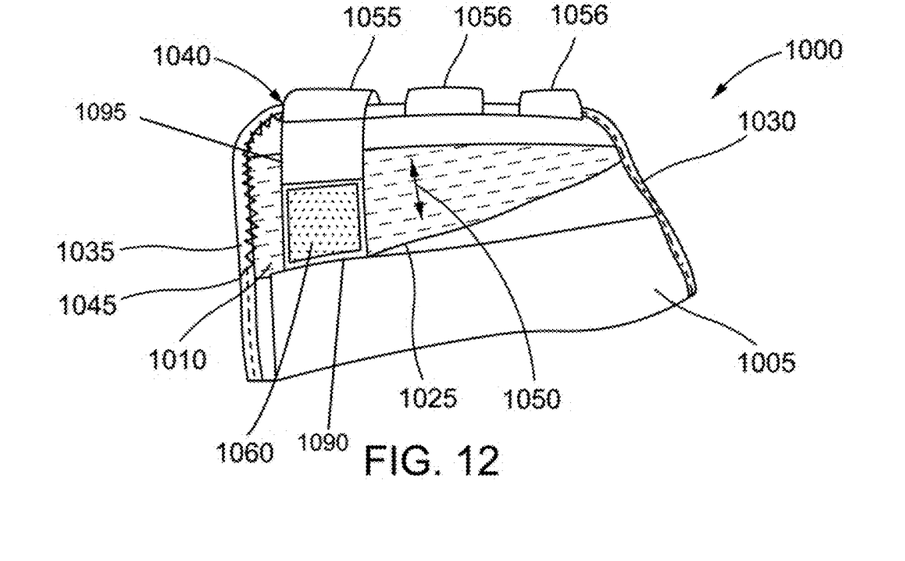
FIG. 12 illustrates the expansion of the region when the attachment members are pulled of the exemplary wrist brace.

When the user pulls on at least one of the free end of attachment members 1056 or 1055, the region 1010 will expand since the first end of attachment members 1056 and/or 1055 are attached to the region 1010. The expansion distance may be relative to the amount of tension applied to the free end of attachment member 1056 and/or 1055 and corresponding closure system. FIG. 12 illustrates the expansion 1050 of the region 1010 when the free end of attachment members 1056 and/or 1055 are pulled. FIG. 12 illustrates the expansion 1050 of the region 1010 when the free end of attachment members 1056 and/or 1055 are pulled of the exemplary wrist brace. As discussed above, the expansion 1050 of the region 1010 may expand up to 100 mm to accommodate a number of different forearm and/or hand sizes.

Figure 13:
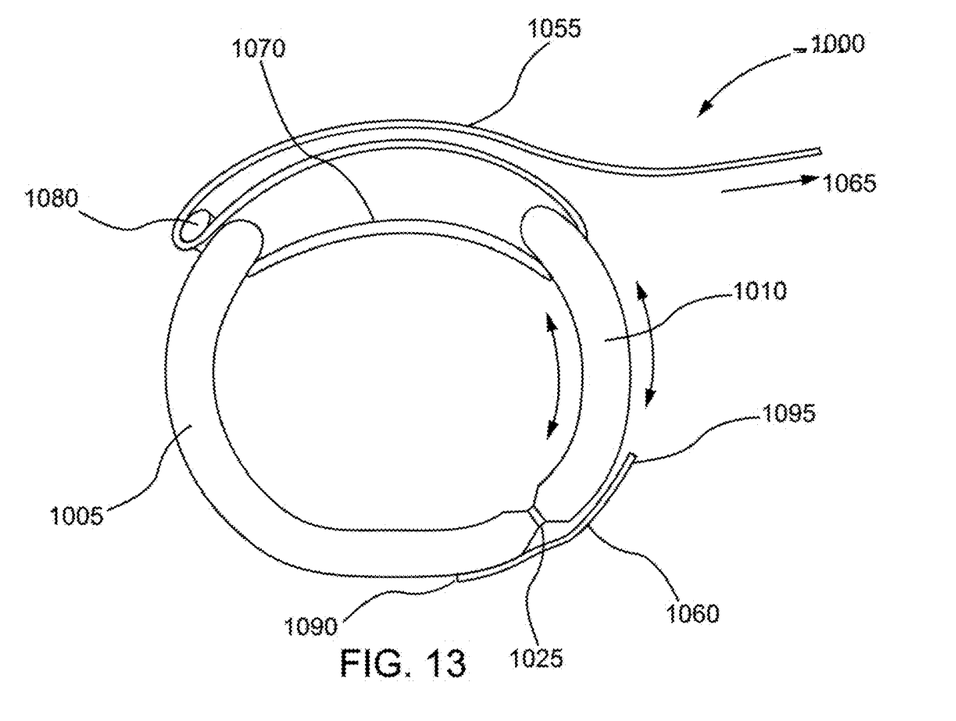
FIG. 13 illustrates a cross section of the exemplary wrist brace 1000 as the stabilizer attachment member receives a pulling motion from a user.

FIG. 13 illustrates a cross section of the exemplary wrist brace 1000 as the stabilizer strap receives a pulling motion from a user. However, one of ordinary skill in the art will also appreciate that a thumb spica could use a similar configuration to the configuration discussed with respect to brace 1000, while providing the same benefit and/or effect. As shown, the closure system as a hook and loop with a D-ring 1080. The free end of stabilizer strap 1055 may receive a pulling action from the user to attach the attachment member to the brace.

As shown, the first end of the stabilizer is configured to the more elastic region 1010 and the first end of the hook section attached to the region 1005. The stabilizer attachment member 1055 may be made of a non-stretch or reduced stretch material for added stability when attached to the wrist brace. The hook section 1060 is also made of a similar non-stretch or reduced stretch material and attached to the region 1005. When the free end of the stabilizer attachment member receives a pull from the user 1065 to tighten the stabilizer attachment member 1055, tension is applied to the first end of the stabilizer attachment member 1055 and the region 1010. The region 1010 will stretch within a predetermined range to accommodate a comfortable size for the user. When the stabilizer attachment member 1055 is taut and the user finds a comfortable fit size for their hand/wrist, the free end of the stabilizer attachment member 1055 is attached by the user to the hook section 1060. However, as discussed above, the same technique may be used for a thumb spica to achieve a proper fit around a user's thumb. The thumb spica may be part of the wrist brace configuration or could be applied to any commonly used wrist brace.

Figure 14:
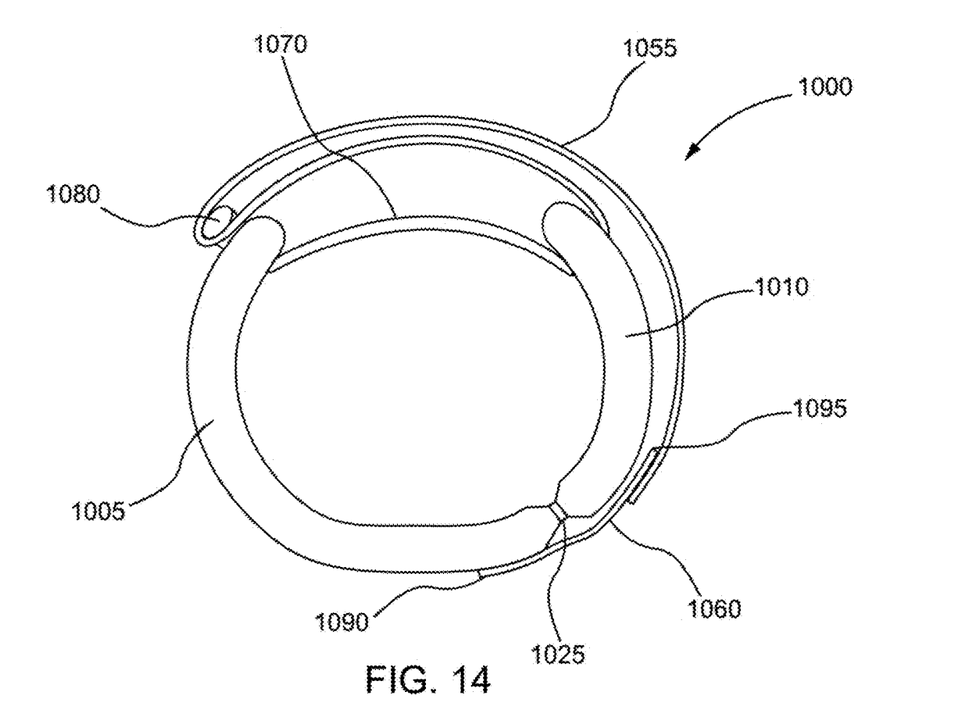
FIG. 14 illustrates the cross section of the exemplary wrist brace or thumb spica with the free end of the stabilizer attachment member attached to the hook section.

FIG. 14 illustrates the cross section of the exemplary wrist brace or thumb spica with the free end of the stabilizer attachment member 1055 attached to the hook section 1060. When the free end of the stabilizer attachment member 1055 is attached to the hook section 1060, the region 1010 is locked at a particular size. The non-stretch or reduced stretch material of the stabilizer attachment member covers the distance of the dorsal locator and the region 1010. As a result, the region 1010 will not stretch or have little stretch due to the stabilizer attachment member 1055 surrounding the region 1010. Thus, the region 1010 regains its stability when the stabilizer attachment member 1055 is attached to the hook section 1060, which disables the adjustability of the region 1010 and fixes it at a size/stretch within a predetermine range.

Figure 15:
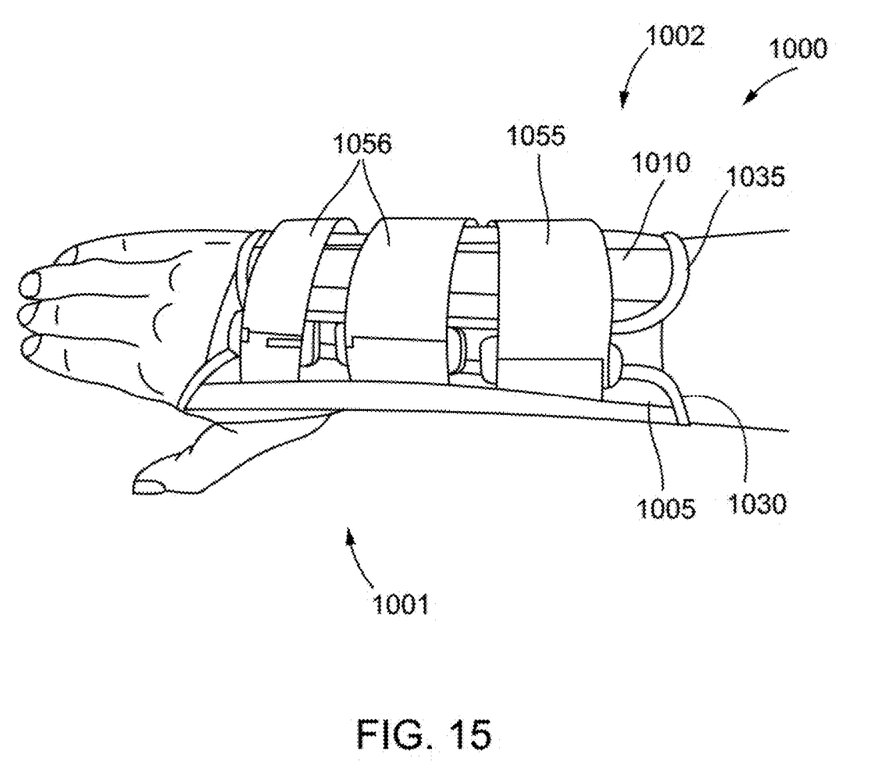
FIG. 15 illustrates the exemplary wrist brace after the stabilizer attachment member is attached to the hook section.

FIG. 15 illustrates the exemplary wrist brace 1000 after the stabilizer attachment member is attached to the hook section 1060. The attachment members 1056 and 1055 may be applied in any order. As shown, the attachment members 1056 attach to the ulnar side 1002, while the stabilizer attachment member surrounds the ulnar side 1002 before being attached to the hook section 1060 in reference to FIG. 14. Since the stabilizer attachment member is made of non-stretch or reduced stretch material, the region 1010's expansion is now limited so that the user's wrist may be stabilized, while still easily accommodating differences in sizes from one user to the next. In other words, the elastic region 1010 expands when the brace is put on the user's wrist and the attachment members 1056 and/or 1055 are pulled. At this point, the brace should be fit to the user's wrist. Accordingly, the stabilizer attachment member 1055 then wraps around the elastic region 1005 so that it is no longer able to stretch and locks the elastic region 1010 so that the user's wrist is stabilized. At the same time a comfortable fit around the user's forearm and/or hand is also achieved with minimal effort and a simplified design.

Figure 16:
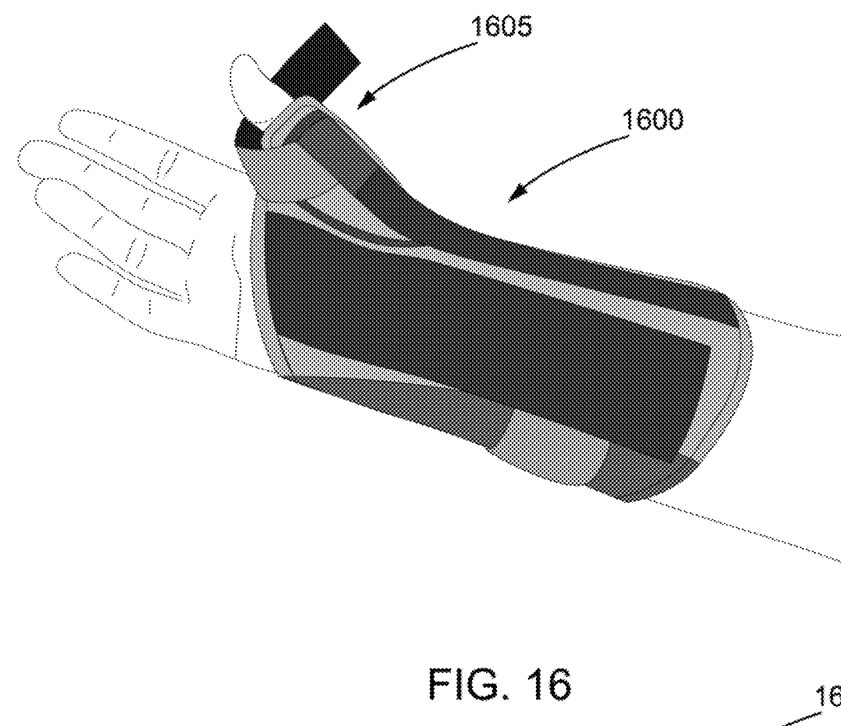
FIG. 16 illustrates a exemplary thumb spica including a thumb support for supporting a user's thumb.

FIG. 16 illustrates a exemplary thumb spica 1600 including a thumb support 1605 for supporting a user's thumb. As shown, the thumb support 1065 includes a stabilizer attachment member 1610, which utilizes a similar configuration to that described with respect to FIGS. 13 and 14.

Referring back to FIGS. 2-9, in connection with FIG. 16, by splitting the region 205 from region 210 at the point 225, the wrist brace and thumb spica 1600 are able to function properly by keeping the radial region 201 stable. This allows the thumb and thumb area at the radial side 201 to be held more securely. The region 205 is more stable because of the no stretch or reduced stretch materials. Areas with more stretch generally have less stability. Sectioning the region 210 on the ulnar side 202 will allow the region 210 to have greater flexibility and stretch for the sizing without affecting the strength of the radial side 201.

Specifically, a user can size the thumb spica easily by pulling on the attachment member 1610 which pulls elastic region 1620, which allows the thumb spica to easily conform to the user's thumb size without becoming a cumbersome process. The elastic region 1620 performs similarly to region 1010 ref FIG. 13 and FIG. 14.

Figure 17:
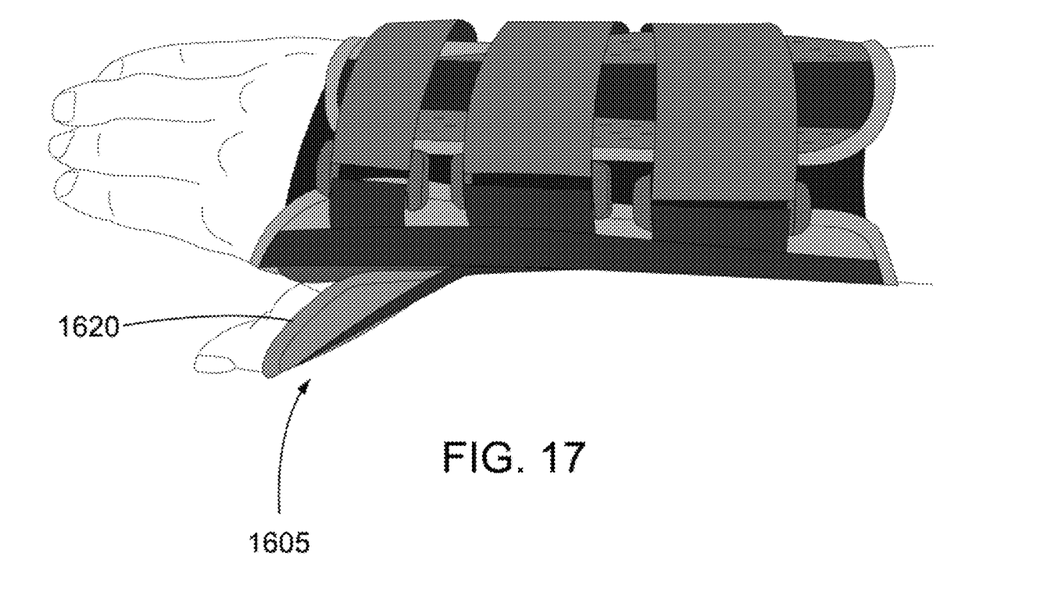
FIG. 17 illustrates the exemplary thumb spica with an elastic region

FIG. 17 illustrates the exemplary thumb spica with an elastic region. As shown, the user's thumb is now supported by the thumb support 1605. Additionally, the thumb support easily conforms to the user's thumb size by using the mechanism described with respect to FIGS. 13 and 14. Thus a proper fit is ensured without the difficulties of obtaining the correct fit seen in the prior art.

Figure 18:
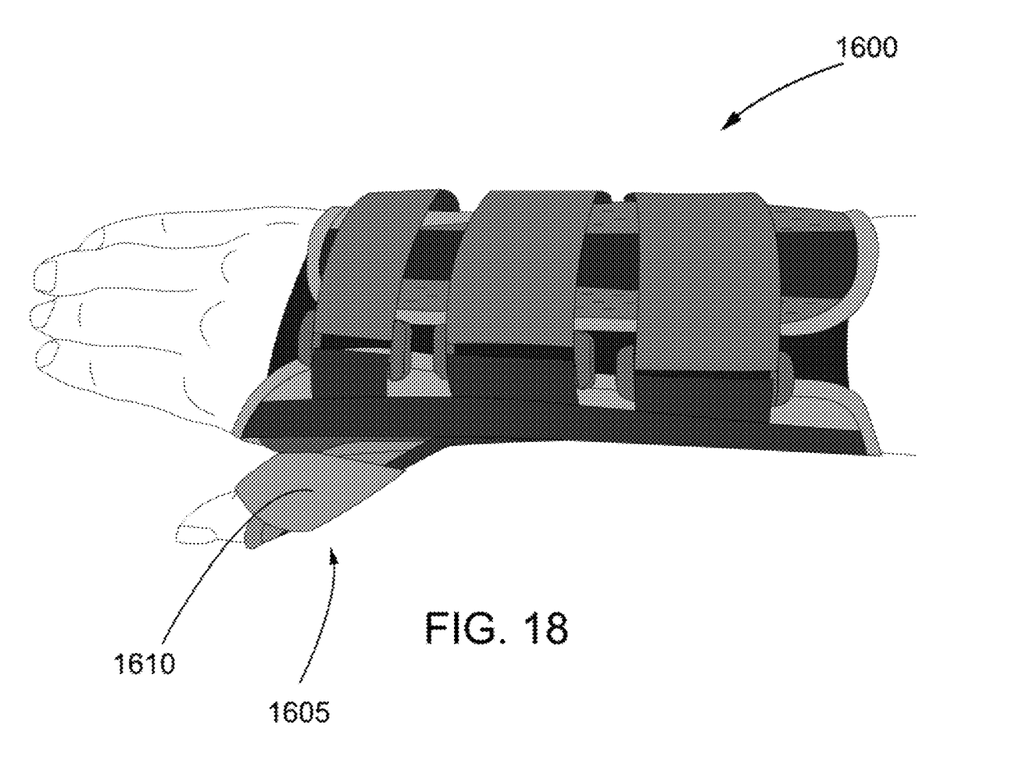
FIG. 18 illustrates the thumb spica of FIG. 17 after the stabilizer attachment member has been affixed around a user's thumb.

FIG. 18 illustrates the thumb spica of FIG. 17 after the stabilizer attachment member has been affixed around a user's thumb. As shown in FIG. 18, once the stabilizer attachment member 1610 is wrapped around the thumb support 1605, the user's thumb is stabilized and comfortably fit to the orthopedic brace.

Figure 19:
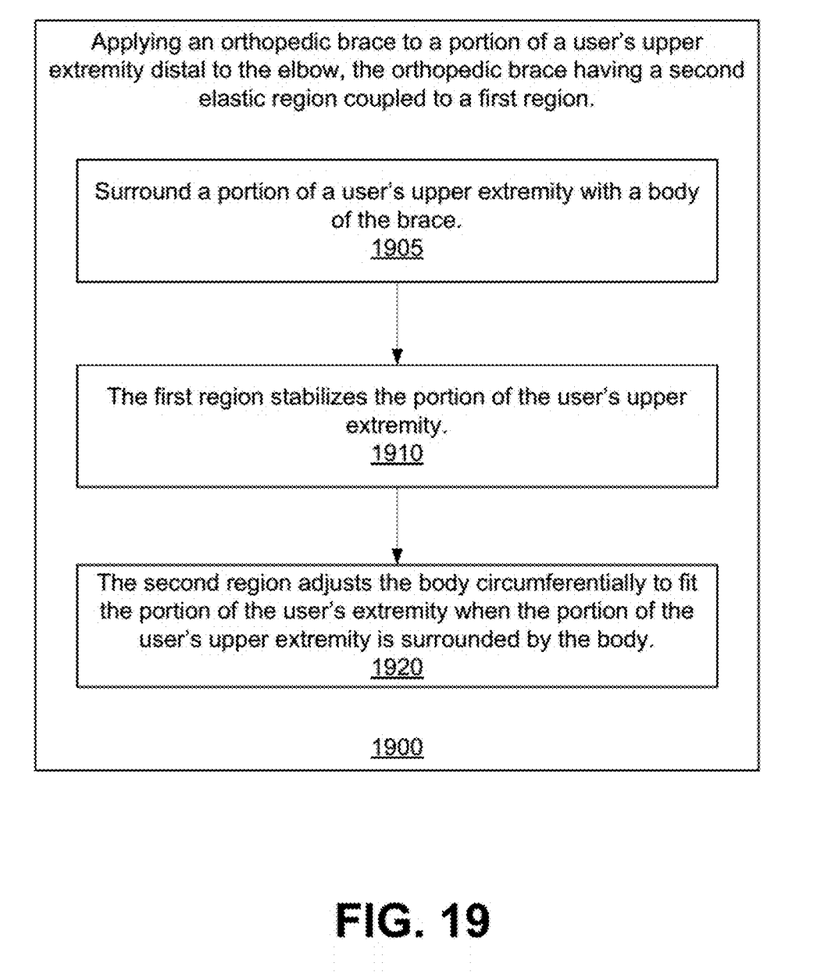
FIG. 19 conceptually illustrates a process for applying an orthopedic brace to a portion of a user's upper extremity distal to the elbow.

FIG. 19 conceptually illustrates a process 1900 for applying an orthopedic brace to a portion of a user's upper extremity distal to the elbow. In the process 1900, the orthopedic brace may include a body having a first region to stabilize the portion of the user's upper extremity and second region coupled to the first region. Additionally, the second region may have sufficient elasticity to enable the body to adjust circumferentially to fit said portion of the user's upper extremity.

As shown, the process 1900 surrounds (at 1905) the portion of the user's upper extremity with the body. The first region (at 1910) stabilizes the portion of the user's upper extremity. The second region (at 1920) adjusts the body circumferentially to fit the portion of the user's upper extremity when the portion of the user's upper extremity is surrounded by the body.

It is to be understood that the specific order or hierarchy of steps in the methods or processes disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The various aspects of a fixating support presented throughout this disclosure are provided to enable one of ordinary skill in the art to practice the present invention. Various modifications to aspects presented throughout this disclosure will be readily apparent to those skilled in the art, and the concepts disclosed herein may be extended to other flexible supports. Thus, the claims are not intended to be limited to the various aspects of this disclosure, but are to be accorded the full scope consistent with the language of the claims. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, or any applicable analogous statute or rule of law in any jurisdiction, unless the element is expressly recited using the phrase "means for" or, in the case of a method claim, the element is recited using the phrase "step for."

What is claimed is:

1. A circumferentially expandable wrist brace for accommodating a plurality of wrist sizes, comprising:
    a wrist brace body defining a radial region and an ulnar region, the radial region and the ulnar region each having a proximal edge and a distal edge, the radial region including a thumb hole and having a first material applied to its upper and lower surface to establish an elasticity of the radial region, and the ulnar region having a second material applied to its upper and lower surface to establish an elasticity of the ulnar region, the elasticity of the ulnar region being greater than the elasticity of the radial region, and the proximal edge of the ulnar region, which is directly adjacent the proximal edge of the radial region, has a length that is greater than a length of the distal edge of the ulnar region, said distal edge of the ulnar region being directly adjacent the distal edge of the radial region;
    an adjustment strap attached at a first end to an interior of the ulnar region; and
    a non-elastic locking strap attached at a first end at a juncture of the radial region and ulnar region;
    wherein the wrist brace stretches circumferentially to a greater extent adjacent the proximal edge compared to a circumferential stretch at the distal edge.

2. The circumferentially expandable wrist brace of claim 1, wherein the first and second materials are laminated onto the radial and ulnar regions, respectively.

3. The circumferentially expandable wrist brace of claim 1, wherein the wrist brace expands circumferentially between five and one hundred millimeters from an unstretched state.

4. The circumferentially expandable wrist brace of claim 1, further comprising stitching around a perimeter of the wrist brace body, the stitching comprising an elastic thread.

5. The circumferentially expandable wrist brace of claim 1, further comprising a first binding around a peripheral edge of the radial region, and a second binding around a peripheral edge of the ulnar region, the second binding having a greater elasticity than the first binding.

6. The circumferentially expandable wrist brace of claim 1, wherein the ulnar region includes an expansion area that continuously narrows in the proximal to distal direction.

* * * * *